(12) United States Patent
Lee

(10) Patent No.: US 7,060,478 B2
(45) Date of Patent: Jun. 13, 2006

(54) PROCESS FOR PREPARING LYSOZYME

(76) Inventor: Min-Hsiung Lee, No. 1. Sec. 4, Roosevelt Rd., Da-an District, Taipei City (TW)

( * ) Notice: Subject to any disclaimer, the term of this patent is extended or adjusted under 35 U.S.C. 154(b) by 0 days.

(21) Appl. No.: 10/798,259

(22) Filed: Mar. 12, 2004

(65) Prior Publication Data

US 2005/0202546 A1  Sep. 15, 2005

(51) Int. Cl.
*C12N 9/00* (2006.01)
*C12N 9/14* (2006.01)
*C12N 9/96* (2006.01)

(52) U.S. Cl. ............... 435/195; 435/183; 435/188; 435/815; 435/816

(58) Field of Classification Search ........... 435/183
See application file for complete search history.

(56) References Cited

U.S. PATENT DOCUMENTS

| | | | |
|---|---|---|---|
| 3,767,531 A * | 10/1973 | Olson et al. | 435/180 |
| 3,909,358 A * | 9/1975 | Stanley et al. | 435/178 |
| 4,532,212 A * | 7/1985 | Odell | 435/197 |
| 4,839,419 A * | 6/1989 | Kraemer et al. | 525/54.1 |
| 5,075,430 A * | 12/1991 | Little | 536/25.41 |

OTHER PUBLICATIONS

Alderton et al., Isolation of lysozyme from egg white, J. Biol. Chem., 1945, pp. 43-57.*

* cited by examiner

*Primary Examiner*—David M. Naff
*Assistant Examiner*—Deborah K. Ware
(74) *Attorney, Agent, or Firm*—Birch, Stewart, Kolasch & Birch, LLP

(57) ABSTRACT

A process for preparing lysozyme is provided which is characterized by mixing the egg white or its diluted solution with diatomaceous earth, kaolin, zeolite, or the mixtures thereof, and followed by eluting the adsorbed lysozyme with a salt solution. The diatomaceous earth, kaolin, and zeolite can specifically adsorb the lysozyme in egg white, and the adsorbed lysozyme can be easily eluted with a salt solution. According to the process of the present invention, the lysozyme in egg white can be easily and effectively isolated.

7 Claims, 4 Drawing Sheets

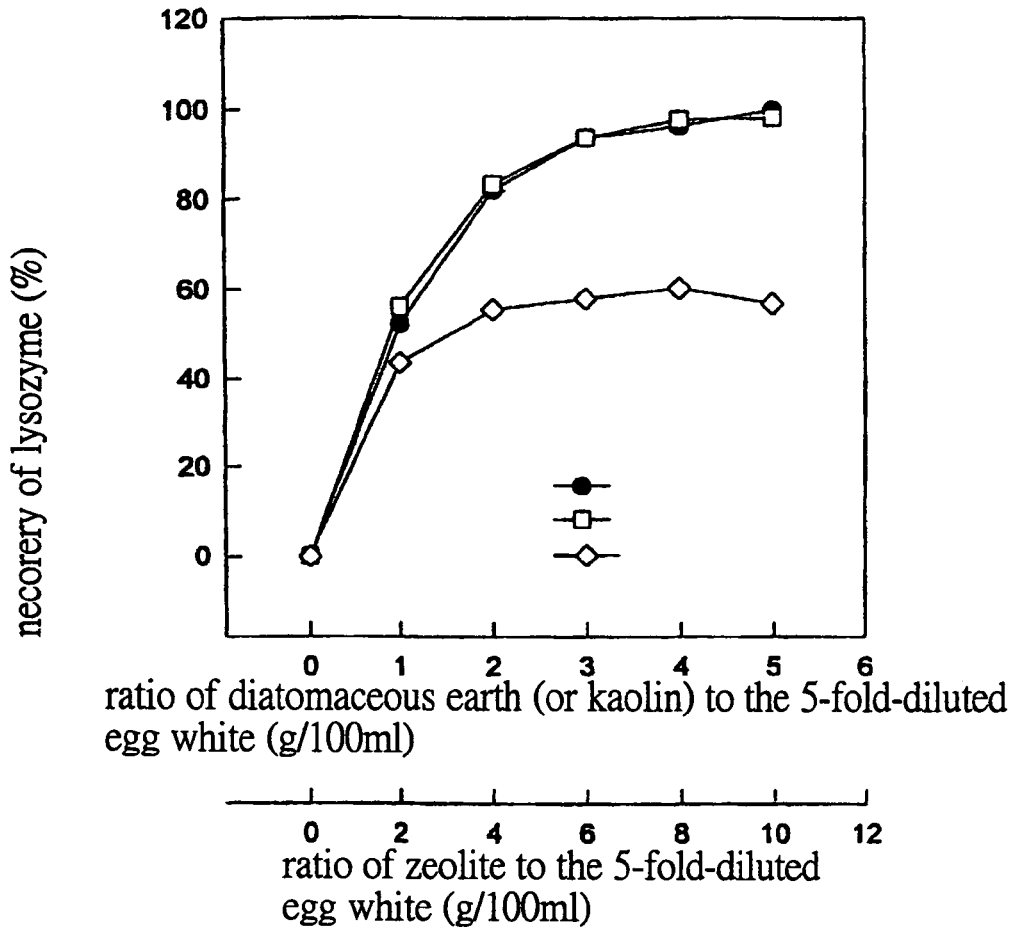
Fig. 1 Effect of the amount of various adsorbents on the recovery rates of lysozyme from egg white.

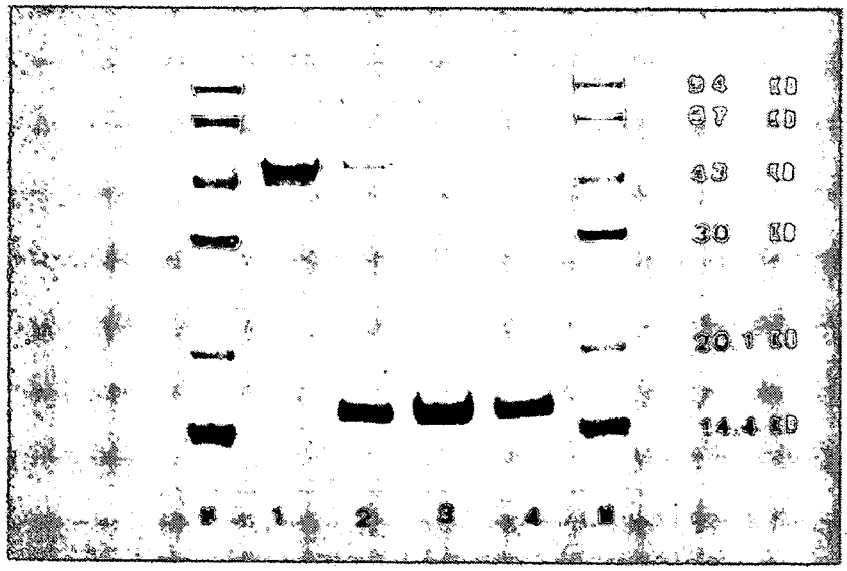

Fig. 2 The SDS-PAGE spectra of the original egg white, and the lysozyme products prepared by using the three different kinds of adsorbents M: protein markers
Lane 1: the original egg white
Lane 2: the lysozyme product obtained by treating the egg white with diatomaceous earth
Lane 3: the lysozyme product obtained by treating the egg white with kaolin
Lane 4: the lysozyme product obtained by treating the egg white with zeolite

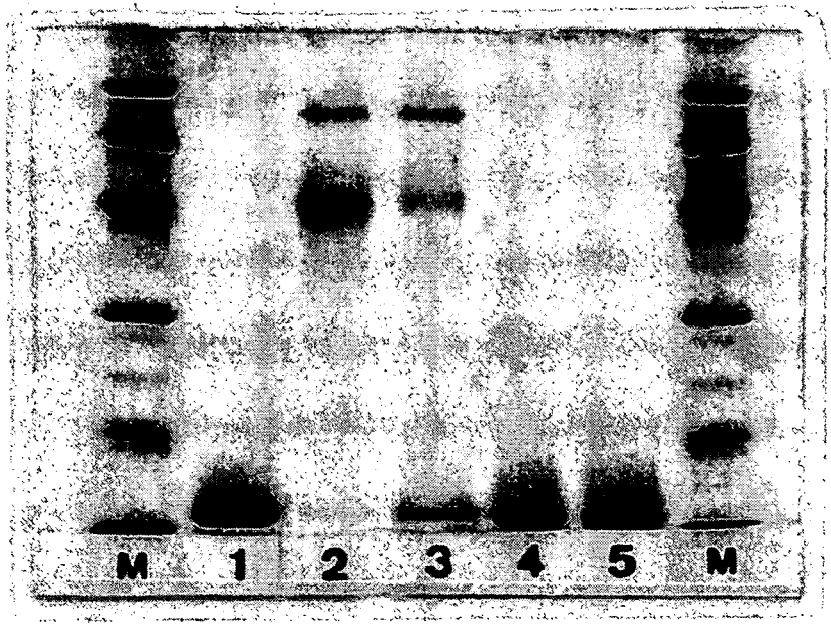

Fig. 3 The SDS-PAGE spectra of the lysozyme standard and various purified lysozyme products M: protein markers
Lane 1: lysozyme standard (Sigma Co.)
Lane 2: the original egg white
Lane 3: the lysozyme product obtained by treating the egg white with kaolin
Lane 4: the lysozyme crystals obtained by crystallization of the product of Lane 3
Lane 5: the purified lysozyme obtained by subjecting the product of Lane 3 to anion exchange treatment with Amberlyst A-27.

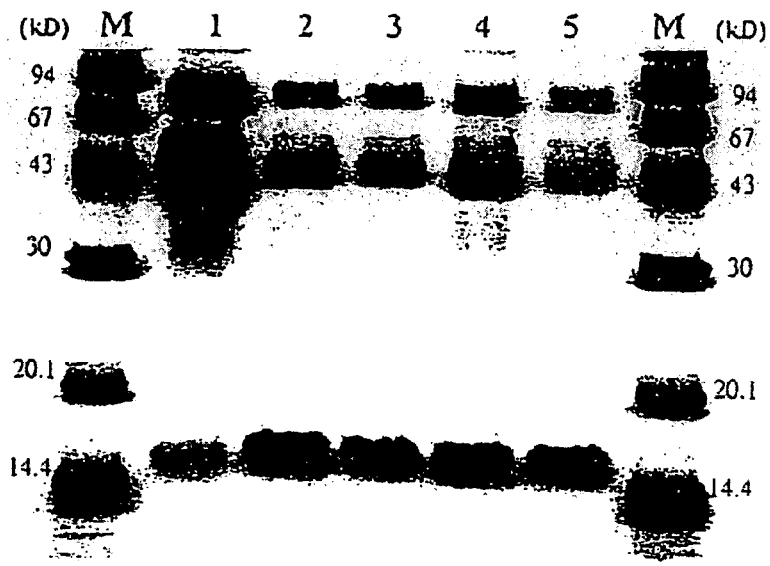

Fig. 4 The SDS-PAGE spectra of the original egg white and the various lysozyme products obtained in Examples 7 and 8

M: protein marker
Lane 1: original egg white
Lane 2: product obtained by using the undiluted original egg white as the starting material
Lane 3: product obtained by using the egg white diluted with 3 volumes of water as the starting material
Lane 4: product obtained by using the egg white diluted with 5 volumes of water as the starting material
Lane 5: product obtained by using the egg white diluted with 3 volumes of water as the starting material and eluted with 4% KCl solution instead of 4% NaCl solution.

PROCESS FOR PREPARING LYSOZYME

FIELD OF THE INVENTION

The present invention relates to a convenient and effective process for preparing lysozyme.

BACKGROUND OF THE INVENTION

Lysozyme is widely used in food and pharmaceutical treatment. Lysozyme is commonly applied in food preservation and processing, including aquatic products such as oysters, shrimp, and the like; fresh foods such as bean curds, vegetables, fish, fruits, and the like; and processed food such as sushi, cooked noodles, fish balls, meat balls, fish flakes, and the like. In addition, lysozyme is widely applied in the manufacture of cheese. Lysozyme has the same role as rennet which makes casein in the milk unstable to form curd.

Pure lysozyme is also used as an effective ingredient for preparing medicine. For example, lysozyme is used in a medicine for treating the wounds of chronic rhinitis or as a preserving agent for pharmaceutical products such as eye drops.

Chicken egg white containing about 3.5% lysozyme (based on dry weight) is the main material for preparing lysozyme. At present, the primary industrial method for preparing lysozyme is direct crystallization [Alderton, G. and Fevold, H. L. Direct crystallization of lysozyme from egg white and some crystalline salts of lysozyme. J. Biol. Chem. 104:1(1946)]. This method involves adding 5% sodium chloride to the chicken egg white liquid, adjusting the pH level to 9.5, adding a small amount of crystal seeds, and crystallizing at 4° C. for about 5 days. The recovery rate of lysozyme is about 60 to 80%. However, the recovery rate for this method may significantly vary depending on the treating amount of raw material. Chiang et al. [Chiang et al., Research on purifying lysozyme from chicken egg white by ultrafiltration, J. Chin. Agric. Chem. 24(1): 86(1986), Taipei] conducted an experiment in the same manner using 700 mL of chicken egg white liquid, and found that the recovery rate for a single crystallization was 43.0%, and the purification efficiency was 4.9 fold; the recovery rate after double crystallization dropped to 12.4%, and the purification efficiency is 7.9 fold; the recovery rate after triple crystallization was 11.8%, and the purification efficiency was 9.1 fold. The results show that the recovery rate was significantly reduced, and the purification efficiency was still not satisfactory after many operations. Furthermore, a great disadvantage was that the large amount of egg white liquid used in the process contained a high concentration of sodium chloride after the separation of lysozyme. Therefore, the recovered egg white liquid could not be effectively used any more after the separation. To address this problem, many researchers tried preparing lysozyme by ultrafiltration. The research of Chiang et al. (the same research as above) showed that the recovery rate for a single ultrafiltration accompanied with crystallization was 47%, and the purification efficiency was 3.0 fold. Chiang et al. disclosed that the lysozyme recovery rate after ultrafiltration by using a membrane with a molecular weight cut-off of 30,000 was 96%, and the purification efficiency was only 6 fold, indicating that the purification effect was not satisfactory [Chiang, B. H., et al. Egg White lysozyme purification by ultrafiltration and affinity chromatography, J. Food Sci. 58(2): 303(1993)]. Furthermore, the great disadvantage of the ultrafiltration method was that the filter membrane was easily blocked, and thus mass production becomes difficult.

In addition, there is a method for purifying lysozyme by using an adsorbent. Alderton et al. [Alderton, et al. Isolation of lysozyme from egg white, J. Biol. Chen. 157: 43(1945)] disclosed that bentonite has the property of adsorbing lysozyme, but was not easily eluted. It needs to be eluted with a solution containing 5% acetic acid in pyridine. As a result, this method was not suitable for industrial production.

Therefore, the present inventor have undertaken extensive studies in order to solve the above-mentioned problems and found that diatomaceous earth, kaolin, and zeolite could specifically adsorb the lysozyme, and the adsorbed lysozyme could be easily eluted with a salt solution. Furthermore, the unadsorbed egg white has the same processing properties as the original egg white. Meanwhile, the unadsorbed egg white liquid is not contaminated by any chemicals. Therefore, it can be directly used in food processing as the original egg white. The present invention has been accomplished based on the above finding.

BRIEF DESCRIPTION OF THE DRAWINGS

FIG. 1 shows the effect of the amount of various adsorbents on the recovery rate of lysozyme from egg white.

FIG. 2 shows the SDS-PAGE spectra of the original egg white liquid, and the lysozyme products prepared by using three kinds of adsorbents, wherein:
M: protein marker;
Lane 1: the original egg white
Lane 2: the lysozyme product obtained by treating the egg white with diatomaceous earth;
Lane 3: the lysozyme product obtained by treating the egg white with kaolin; and
Lane 4: the lysozyme product obtained by treating the egg white with zeolite.

FIG. 3 shows the SDS-PAGE spectra of the lysozyme standard and the various lysozyme products, wherein:
M: protein marker;
Lane 1: the lysozyme standard;
Lane 2: the original egg white;
Lane 3: the lysozyme product obtained by treating the egg white with kaolin;
Lane 4: the lysozyme product obtained by crystallization of the product of Lane 3; and
Lane 5: the purified lysozyme obtained by subjecting the product of Lane 3 to anion exchange treatment with Amberlyst A-27.

FIG. 4 shows the SDS-PAGE spectra of the original egg white and the various lysozyme products obtained in Examples 7 and 8, wherein:
M: protein marker;
Lane 1: the original egg white;
Lane 2: lysozyme product obtained by using the undiluted original egg white as the starting material;
Lane 3: lysozyme product obtained by using the egg white diluted with 3 volumes of water as the starting material;
Lane 4: lysozyme product obtained by using the egg white diluted with 5 volumes of water as the starting material; and
Lane 5: lysozyme product obtained by using the egg white diluted with 3 volumes of water as the starting material and eluted with 4% KCl solution instead of 4% NaCl solution.

ANALYSIS METHOD

1. Determination of the Relative Amount of Protein

After the protein solution was property diluted, the absorbance ($A_{280}$) at 280 nm was measured with a U-1100

Spectrophotometer manufactured by Hitachi Co. The adsorption % of protein was calculated from the relative value of $A_{280}$.

2. Determination of the Protein Concentration

The Lowry method was used for the determination of protein concentration.

A solution: 10 gm of $Na_2CO_3$ and 2 gm of $NaHCO_3$ were dissolved in distilled water to make a 500 mL aqueous solution.

B solution: 1.6 gm of $CuSO_4 \cdot 5H_2O$ and 2.3 gm of sodium citrate were dissolved in distilled water to make a 200 mL aqueous solution.

C solution: 50 mL of A solution was mixed with 1 mL of B solution before use.

Folin-Ciocalteu's phenol reagent: 2 volumes of distilled water were added to 1 volume of the phenol reagent before use.

0.2 mL of properly diluted sample solution was added to 1 mL of C solution, mixed homogenously, and reacted for 30 minutes at room temperature. Next, 0.1 mL of Folin's solution was added thereto, and reacted for 60 minutes at room temperature. The absorbance at 650 nm was measured, and the protein content 9 in the sample was calculated by comparing with standard curve.

The standard curve was conducted with 50 to 400 µg/mL of bovine serum albumin as the standard solution.

3. Determination of Lysozyme Activity

*Micrococcus lysodeikticus* biomass was suspended in 0.067 M of phosphate buffer (20 mg/100 mL, pH value 6.3). 2.97 mL of biomass solution was placed in a quartz tube, 3 µL of enzyme solution was added thereto, followed by mixing homogeneously. The absorbance at 450 nm was continuously measured at the room temperature, and the measurements were recorded in 30-second intervals for 20 minutes.

One unit of lysozyme activity in one milliliter solution was defined as the enzyme amount required to reduce 0.001 unit of absorbance per minute under the above conditions.

$$U/mL = \frac{\Delta OD/min}{0.001\ OD/min \times 0.03\ mL}$$

4. SDS-PAGE Electrophoresis

The gel concentration of the separating gel was 15%, and the gel concentration of the stacking gel was 4%. 10 µl of sample buffer solution (note 1) and 4 µl of tracking dye solution (note 2) were added to 10 µl of sample solution (ca.4 mg/mL). The resultant solution was heated at 100° C. for 5 minutes, then, after cooling to room temperature, it was subjected to electrophoresis. The protein band in the gel was dyed with Coomassie Brilliant Blue R, and decolored with acetic acid-methanol-water (10:20:70) until the background became transparent. The gel sheet was then dried for preservation.

Note 1: SDS-PAGE Sample Buffer Solution (2×)

| | |
|---|---|
| Tris (Trizma Base, 125 mM × 2) | 3.0 gm |
| EDTA-2Na (2 mM × 2) | 14.8 gm |
| SDS (2% × 2) | 4.0 gm |
| 2-mercaptoethanol (5% × 2) | 10.0 ml |

The ingredients were dissolved with 80 ml of water, and the pH was adjusted to 6.8 then water was added to 100 ml. Then, the solution was diluted 2-fold with distilled water for use.

Note 2: Tracking Dye Solution:

1 mg of bromophenol blue was dissolved in 5 ml of water, and 5 ml of glycerin was added thereto, and mixed homogeneously.

5. Determination of the Functionality of the Unadsorbed Egg White (A) Determination of Foam Expansion and Foam Stability 50 ml of the unadsorbed egg white solution was placed into a 100 ml cylinder, sealed with a wax paper, and vertically shaken for 1 minute (2 times/second). The measured foam volume (mL) represented foam expansion. After settling still for 30 minutes, the remaining foam volume was measured. The ratio percentage of the remaining volume to the original volume represented the foam stability.

(B) Determination of the Emulsion Stability of Egg White 25 ml of unadsorbed egg white solution was placed into a 50 ml cylinder, 25 ml of soybean oil was added thereto and homogenized for 1 minute at 12,000 rpm. The volume (Vo) of the aqueous layer was immediately measured, and then the contents were allowed to settle for 30 minutes. Then, the volume (Vt) of the aqueous layer was measured again. The emulsion stability of the egg white was measured according to the following equation:

$$\text{Emulsion stability (\%)} = \frac{50 - Vt}{50 - Vo} \times 100\%$$

EXAMPLES AND TEST EXAMPLES

The following examples and test examples are intended to further illustrate the present invention and are not intended to limit the scope of the invention.

Example 1

The chicken egg white was diluted with 4 volumes of distilled water and mixed gently. The mixture was filtered through a multi-layer gauze to remove the sticky mass substance to obtain the egg white solution. Five grams of different adsorbents (bentonite, diatomaceous earth, kaolin, and zeolite manufactured by Sigma Co.) were separately added to each 100 ml of the above egg white solution, and mixed for 30 minutes at room temperature with occasionally shaking. Centrifugation (1,000 g×5 min) was conducted, and the supernatants were separated. The lysozyme activity and the absorbance at 280 nm of the supernatants and the original egg white were measured. The percentages of adsorbed egg white, the adsorbed lysozyme activities, and the theoretical purification efficiency were calculated based on the determined values of the supernatants. The results are shown in Table 1.

TABLE 1

| Adsorbent | supernatant | | Calculated adsorbed protein | | |
| --- | --- | --- | --- | --- | --- |
| | unadsorbed egg white percentage (%) | unadsorbed lysozyme percentage (%) | adsorbed egg white adsorption (%) | adsorbed lysozyme percentage (%) | lysozyme purification efficiency (fold) |
| Original egg white | 100 | 100 | — | — | — |
| bentonite | 47.18 | 0 | 52.82 | 100 | 1.89 |
| diatomaceous earth | 96.73 | 0 | 3.27 | 100 | 26.88 |
| kaolin | 94.02 | 0 | 5.98 | 100 | 16.72 |
| zeolite | 95.82 | 49 | 4.18 | 51 | 12.20 |

Table 1 shows that although the adsorption of lysozyme by bentonite was very high, the adsorption of proteins other than lysozyme was also high. As a result, the adsorption specificity was very poor. The calculated purification fold for lysozyme specific activity was only increased 1.89 fold. In contrast, the egg white adsorbed by diatomaceous earth, kaolin and zeolite were very specific to lysozyme. The lysozyme specific activities increased 26.88 fold, 16.72 fold and 12.20 fold, respectively. The results reveal that diatomaceous earth, kaolin, and zeolite have an excellent adsorption ability specific to lysozyme. Therefore, the above three kinds of adsorbents should be able to be effectively applied in the preparation of lysozyme.

Example 2

Each 100 mL egg white solution as prepared in Example 1 was, separately, subjected to adsorption treatment with 5 gm of bentonite, diatomaceous earth, kaolin and zeolite in the same manner as Example 1. The lysozyme activity of each supernatant was determined, and thereby the adsorbed lysozyme percentage was calculated. Furthermore, the adsorbed lysozyme was eluted from each precipitated adsorbent with 100 mL of 1M NaCl at room temperature by shaking for 30 minutes at 75 rpm. Each eluate was collected by centrifugation, and the lysozyme activity in each elute was determined. The lysozyme recovery rate after the treatment with each adsorbent and the elution rates of the adsorbed lysozyme from each adsorbent were calculated. The results are shown in Table 2.

TABLE 2

The purification efficiency of lysozyme from egg white by adsorption with various adsorbents.

| Adsorbent | Percentage of adsorbed lysozyme (%) | Recovery rates of lysozyme (%) | Elution rates of adsorbed lysozyme from adsorbent (%) |
| --- | --- | --- | --- |
| Bentonite | 100 | 0 | 0 |
| Diatomaceous earth | 100 | 82.23 | 82.23 |
| Kaolin | 100 | 90.7 | 90.7 |
| Zeolite | 50.88 | 49.05 | 96.4 |

Table 2 shows that the adsorption of lysozyme on bentonite was very strong, and the adsorbed lysozyme could not be eluted with 1 M NaCl. On the other hand, the lysozyme separately adsorbed by diatomaceous earth, kaolin, and zeolite used in the present invention was easily eluted. The elution rates for diatomaceous earth, kaolin, and zeolite were 82.23%, 90.70%, and 96.40%, respectively. The recovery rates of lysozyme were 82.23%, 90.70% and 49.05%, in that order.

Example 3

One to five grams of diatomaceous earth or kaolin, or 2 to 12 grams of zeolite were, separately, added to each 100 mL of egg white solution as prepared in Example 1. Each mixture was processed in the same manner as in Example 1. The adsorbed lysozyme was eluted from each adsorbent with 10 mL of 1M NaCl (75 rpm, 30 min., 25° C.). Each eluate was centrifuged and collected, and the recovery rate of lysozyme activity was determined. As shown in FIG. 1, almost 100% of the lysozyme was recovered by using only 4 gm of diatomaceous earth or kaolin for each 100 mL egg white solution (i.e. the ratio of the original egg white to the adsorbent was 10:1). On the other hand, when zeolite was used as the adsorbent, the maximum lysozyme recovery (ca. 50%) was obtained by using 8 gm of zeolite (i.e. the ratio of the original egg white to the adsorbent was 5:1).

Example 4

Four grams of diatomaceous earth or kaolin, or 8 gm of zeolite were, separately, added to each 100 mL egg white solution as prepared in Example 1. Each mixture was processed in the same manner as in Example 1, except that the eluent used was changed to NaCl solutions of various concentrations. The recovery rate of lysozyme in the eluate was determined and is shown in Table 3. Table 3 shows that most of the adsorbed lysozyme was recovered by eluting with 1M of NaCl. The lysozyme activity recovery rate by using diatomaceous earth, kaolin and zeolite was 86.01%, 90.12% and 51.69%, respectively.

TABLE 3

Effect of the concentration of sodium chloride on the elution of lysozyme from various adsorbents.

| NaCl concentration (M) | Lysozyme recovery rates (%) | | |
| --- | --- | --- | --- |
| | Diatomaceous earth | Kaolin | zeolite |
| 0 | 0 | 0 | 0 |
| 0.25 | 27.50 | 29.18 | 34.27 |
| 0.50 | 42 | 58.10 | 42.13 |
| 0.75 | 43.52 | 78.96 | 41.57 |
| 1.00 | 86.01 | 90.12 | 51.69 |

Example 5

Eight grams of diatomaceous earth, 8 gm of kaolin and 16 gm of zeolite were, separately, added to each of 200 mL chicken egg white solution as prepared in Example 1. Each mixture was placed on a water-bath oscillator to undergo adsorption for 30 minutes (75 rpm, 25° C.), and then subjected to centrifugation (1,000 g×5 min). The precipitate was washed with 150 mL of water, and centrifuged. Then, the adsorbed lysozyme was eluted with 150 mL of 1M NaCl three times. The total protein concentration and the lysozyme activity were determined, and electrophoresis was conducted.

As shown in Table 4, the lysozyme recovery rates by using diatomaceous earth, kaolin and zeolite as the adsorbents were 82%, 98% and 54%, respectively, and the purification efficiency was 17.50 fold, 19.91 fold, and 20.85 fold, in that order. The three kinds of adsorbents all manifested excellent purification efficiency.

TABLE 4

The lysozyme activities of the original chicken egg white and the lysozyme products prepared in this invention.

| Treatment | Specific activity (U/mg) | Purification efficiency (fold) | Lysozyme recovery rate (%) |
|---|---|---|---|
| Original egg white | 516 | 1 | — |
| Diatomaceous earth-treated | 8798 | 17.05 | 82 |
| Kaolin-treated | 10273 | 19.91 | 98 |
| Zeolite-treated | 10757 | 20.85 | 54 |

FIG. 2 shows the SDS-PAGE spectra of the lysozyme products purified by using the above three kinds of adsorbents. Lane 1 in FIG. 2 shows the spectrum of the original egg white, the 43 Kd band was the main component, and the 14.4 Kd band of lysozyme was not visible. This spectrum indicated that the lysozyme content in the original egg white was relatively little. Lanes 2, 3, and 4 show the SES-PAGE spectra of the purified lysozyme products treated with diatomaceous earth, kaolin, and zeolite, respectively. Each of the three samples shows that the 14.4 Kd band of lysozyme is the main component, while the main component (43 Kd) in the original egg white is the minor component. The results show that the above three kinds of adsorbents could very exclusively adsorb the lysozyme.

Example 6

The lysozyme was prepared by using kaolin as an adsorbent in the same manner as Example 5. The obtained lysozyme product was then further subjected to anion exchange treatment or the crystallization according to the following methods.

(1) Purification Treatment with Anion Exchange Resin

One gram of anion exchange resin (Amberlyst A-207, OH⁻ type, Organo Co., Japan) was washed with distilled water until its pH was about 8 or 9. Ten milliliters of adsorption-purified, dialyzed enzyme solution was added thereto, and mixed for 1 hour at room temperature. The supernatant was separated, the total egg white concentration and the lysozyme activity of the supernatant were determined, and electrophoresis was conducted.

(2) Crystallization of Lysozyme

The enzyme solution eluted from the kaolin adsorbent was concentrated to about one sixth by volume through ultrafiltration. The pH was adjusted to 9.5, and a small amount of crystalline lysozyme was then added to the enzyme solution and stored at 4° C. to affect crystallization. After 4 days, the crystals of lysozyme were collected by filtration. The protein content and the lysozyme activity were then determined. The protein content and the lysozyme activity before treatment and after treatment were then determined. The specific activity, purification fold of the lysozyme, and the lysozyme recovery rate were calculated. The results are shown in Table 5. The results show that the above-mentioned two kinds of treatments were able to further purify the lysozyme. The purification folds were 28 fold and 27 fold for anion exchange treatment and crystallization, respectively.

The SDS-PAGE electrophoresis of the above-mentioned purified lysozyme products was conducted. The results are shown in FIG. 3. The results show that the lysozyme purified by anion exchange treatment and by crystallization manifests a single band which is the same as that for commercially available purified lysozyme (Sigma Co. P). The results show that the above-mentioned two purified products were both highly purified lysozymes.

TABLE 5

The efficiencies of the lysozyme purification

| Treatment | Specific activity (U/mg) | Purification efficiency (fold) | Recovery rate (%) |
|---|---|---|---|
| Original egg white | 722 | 1 | — |
| Kaolin adsorption purification | 13527 | 18.74 | 88.04 |
| Kaolin adsorption purification + Amberlyst A-27 (OH⁻) treatment | 20375 | 28.22 | 80.98 |
| Kaolin adsorption purification + crystallization | 19724 | 27.32 | 68.27 |

Test Example 1

The processing functionality, i.e. foam expansion, foam stability, and emulsion stability of the three kinds of unadsorbed egg white recovered in the present invention were measured according to the above-mentioned methods, and the results were compared with those of the original egg white. The results are shown in Table 6. Table 6 shows that the unadsorbed egg white recovered from adsorption treatment in this invention still has excellent processing functionalities.

Furthermore, the adsorbents used in the present invention are legal additives used in food processing. The egg white treated with this kind of adsorbents can confidently be used safely. The treated unadsorbed egg white can be widely used as food ingredients because no salts or no other additives are added thereto.

TABLE 6

Comparison of the functionalities of chicken egg white before and after the adsorption treatment.

| | Functionality | | |
|---|---|---|---|
| Sample | Emulsion stability (%) | Foam expansion (mL) | Foam stability (%) |
| Original egg white | 72 | 37.5 | 92 |
| Egg white unadsorbed by diatomaceous earth | 64 | 17.5 | 71.43 |
| Egg white unadsorbed by kaolin | 64 | 21.0 | 29.46 |
| Egg white unadsorbed by zeolite | 72 | 28.5 | 100 |

Example 7

Twenty grams of egg white, 20 gm of egg white diluted with 40 mL of distilled water, and 20 gm of egg white diluted with 80 mL of distilled water were separately mixed with 5 g of kaolin (Sigma Co.). The mixtures were kept at room temperature with occasional shaking for 30 minutes, and were subjected to centrifugation (1000 rpm×10 min.) to separate the supernatants from the precipitates. Each precipitate, after washing with 200 mL of distilled water, was eluted with 60 mL of 4% NaCl solution. Each eluate was collected, and lysozyme specific activity, purification fold, lysozyme recovery rate, and SDS-PAGE were all determined. The results are shown in Table 7. The results indicate that the purification folds were all more than 18 fold, and the lysozyme recovery rates were all more than 90%. The SDS-PAGE spectra is shown in FIG. 4.

TABLE 7

Effect of dilution factor on the purification of lysozyme from egg white.

| Dilution factor (fold) | Specific activity (U/mg) | purification fold | lysozyme recovery rate (%) |
|---|---|---|---|
| 1 (not diluted) | 10062 | 18.6 | 92.6 |
| 3 | 10747 | 19.8 | 97.4 |
| 5 | 11362 | 21 | 96.2 |

The specific activity of the original egg white is 541 U/mg protein.

Example 8

Twenty grams of egg white was diluted with 40 mL of distilled water, and was then treated in the same manner as that in Example 7, except that the eluent was replaced by a 4% KCl solution. The results reveal that the lysozyme purification efficiency was 19.8 fold and the lysozyme recovery rate was 95.4%. The SDS-PAGE spectrum is shown in FIG. 4 (lane 5).

Invention Effect

The three kinds of adsorbents, namely diatomaceous earth, kaolin, and zeolite, used in the present invention have an excellent and exclusive adsorption specific to lysozyme. Therefore, the lysozyme can be simply, conveniently, and effectively prepared by using the three kinds of adsorbents. When the lysozyme is prepared from the chicken egg white by using the above-mentioned three kinds of adsorbents, the specific activity can be significantly raised to more than 17 fold, and the lysozyme recovery rate is high. The lysozyme recovery rate is about 80% or more (when using diatomaceous earth), about 90% or more (when using kaolin), and about 50% or more (when using zeolite), respectively. If the lysozyme is further purified by crystallization or anion exchange treatment, highly purified lysozyme exhibiting a single band in SDS-PAGE analysis is obtained. According to the present invention, the purified lysozyme can be simply, conveniently, and economically prepared. Therefore, the present invention is very useful for industrial production of lysozyme. Furthermore, the recovered unadsorbed egg white is not contaminated by any foreign material. Therefore, the recovered unadsorbed egg white can be directly used in the food industry without causing any environmental pollution.

What is claimed is:

1. A process for preparing lysozyme, which is characterized by mixing an egg white or its diluted solution with diatomaceous earth, kaolin, zeolite or the mixtures thereof, followed by eluting adsorbed lysozyme with a salt solution.

2. The process for preparing lysozyme according to claim 1, wherein the salt solution is a sodium chloride solution.

3. The process for preparing lysozyme according to claim 1, further comprising a step of purification by crystallization.

4. The process for preparing lysozyme according to claim 1, further comprising a step of purification by anion exchange resin treatment.

5. A process for preparing lysozyme, comprising the steps of:
   mixing a solution of egg white with a mixture of diatomaceous earth, kaolin, and/or zeolite;
   adsorbing the egg white solution by the mixture of diatomaceous earth, kaolin, and/or zeolite; and
   eluting and purifying adsorbed lysozyme with a salt solution.

6. The process for preparing lysozyme according to claim 5, wherein the salt solution is a sodium chloride solution.

7. The process for preparing lysozyme according to claim 5, wherein unadsorbed egg white solution is recovered.

* * * * *